United States Patent [19]

Petersen et al.

[11] Patent Number: 5,604,242
[45] Date of Patent: Feb. 18, 1997

[54] HETEROCYCLIC CHEMISTRY

[75] Inventors: Hans Petersen, Vanløse; Knud E. Andersen, Smørum; Per O. Sørensen, Frederiksberg; Jesper Lau, Farum; Behrend F. Lundt, Kokkedal, all of Denmark

[73] Assignee: Novo Nordisk A/S, Bagsvaerd, Denmark

[21] Appl. No.: 263,641

[22] Filed: Jun. 22, 1994

[30] Foreign Application Priority Data

Jun. 23, 1993 [DK] Denmark ................... 0746/93

[51] Int. Cl.$^6$ .............. C07D 211/60; C07D 211/68; C07D 211/80
[52] U.S. Cl. ............. 514/316; 514/319; 514/330; 546/192; 546/205; 546/206; 546/227
[58] Field of Search ................. 546/227, 192, 546/205, 208; 514/330, 316

[56] References Cited

FOREIGN PATENT DOCUMENTS

| 0346927 | 6/1989 | European Pat. Off. . |
| WO91/07389 | 5/1991 | WIPO . |
| WO92/20658 | 11/1992 | WIPO . |

OTHER PUBLICATIONS

Falch et al., Drug Design and Delivery, vol. 4, pp. 205–215, 1989.
Pavia et al., J. Med. Chem., vol. 35, pp. 4238–4248, 1992.

*Primary Examiner*—C. Warren Ivy
*Assistant Examiner*—Raymond Covington
*Attorney, Agent, or Firm*—Steve T. Zelson, Esq.; Elias J. Lambiris, Esq.

[57] ABSTRACT

The present invention relates to therapeutically active aza-heterocyclic compounds, a method of preparing the same and to pharmaceutical compositions comprising the compounds. The novel compounds are useful in treating a central nervous system ailment related to the GABA uptake.

32 Claims, No Drawings

HETEROCYCLIC CHEMISTRY

FIELD OF THE INVENTION

The present invention relates to novel N-substituted azaheterocyclic carboxylic acids and esters thereof in which a substituted alkyl chain forms part of the N-substituent and salts thereof, to methods for their preparation, to compositions containing them, and to their use for the clinical treatment of abnormal function of the γ-aminobutyric acid neurotransmission system.

BACKGROUND OF THE INVENTION

In recent years much pharmacological research concerning γ-aminobutyric acid (hereinafter designated GABA), an inhibitory neurotransmitter in the mammalian central nervous system, has been carried out.

The inhibition of GABA uptake results in enhanced availability of this inhibitory neurotransmitter in the synaptic cleft and thus to increased GABA' ergic activity. Increased GABA'ergic activity can be useful in the treatment, for example of anxiety, pain and epilepsy, as well as muscular and movement disorders (see, for example, P. Krogsgaard-Larsen et al., Progress in Medicinal Chemistry, 1985, 22, 68–112).

A well-known and potent inhibitor of GABA uptake from the synaptic cleft into presynaptic nerve terminals and glial cells is, for example, 3-piperidinecarboxylic acid (nipecotic acid). However, being a relatively polar compound and therefore unable to cross the blood-brain barrier, 3-piperidinecarboxylic acid itself has found no practical utility as a drug.

In U.S. Pat. Nos. 4,383,999 and 4,514,414 and in EP 236342 as well as in EP 231996 some derivatives of N-(4,4-disubstituted-3-butenyl)azaheterocyclic carboxylic acids are claimed as inhibitors of GABA uptake. In EP 342635 and EP 374801, N-substituted azaheterocyclic carboxylic acids in which an oxime ether group and vinyl ether group forms part of the N-substituent respectively are claimed as inhibitors of GABA uptake. Further, in WO 9107389 and WO 9220658, N-substituted azacyclic carboxylic acids are claimed as inhibitors of GABA uptake. EP 221572 claims that 1-aryloxyalkylpyridine-3-carboxylic acids are inhibitors of GABA uptake.

According to Yunger, L. M. et al., J.Pharm.Exp.Ther. 1984, 228, 109, N-(4,4-diphenyl-3-buten-1-yl)nipecotic acid (designated SK&F 89976A), N-(4,4-diphenyl-3-buten-1-yl)guvacine (designated SK&F 100330A), N-(4,4-diphenyl-3-buten-1-yl)-homo-β-proline (designated SK&F 100561) and N-(4-phenyl-4-(2-thienyl)-3-buten-1-yl)nipecotic acid (designated SK&F 100604J) are orally active inhibitors of GABA uptake. These data are summarized in Krogsgaard-Larsen, P. et al., Epilepsy Res. 1987, 1, 77–93.

DESCRIPTION OF THE INVENTION

The present invention relates to novel N-substituted azaheterocyclic carboxylic acids and esters thereof of formula I

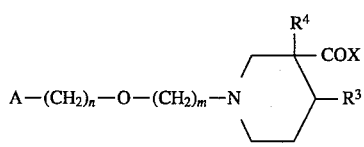

wherein
A is

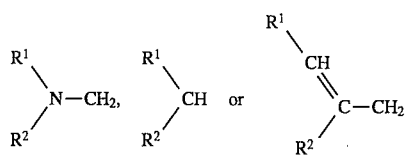

wherein
$R^1$ is a saturated or unsaturated five or six-membered carbocyclic ring optionally substituted with one or two halogen(s), straight or branched $C_{1-4}$-alkyl, phenyl, $C_{1-4}$-alkyl substituted with phenyl or $C_{2-4}$-alkenyl substituted with phenyl which phenyl groups may be optionally substituted with halogen, $C_{1-4}$-alkyl, $C_{1-4}$-alkoxy or trifluoromethyl and which saturated or unsaturated five or six-membered carbocyclic ring may be optionally fused with a benzo ring;

$R^2$ is hydrogen, straight or branched $C_{1-8}$-alkyl, straight or branched $C_{2-8}$-alkenyl, phenyl, $C_{1-4}$-alkyl substituted with phenyl or $C_{2-4}$-alkenyl substituted with phenyl which phenyl groups may be optionally substituted with halogen, $C_{1-4}$-alkyl, $C_{1-4}$-alkoxy or trifluoromethyl;

$R^3$ and $R^4$ each represents hydrogen or may together represent a bond;

X is hydroxy or $C_{1-4}$-alkoxy;

n is 0, 1 or 2;

m is 2, 3 or 4;

provided that $R^1$ and $R^2$ are not at the same time phenyl optionally substituted with halogen, $C_{1-4}$-alkyl, $C_{1-4}$-alkoxy or trifluoromethyl when A is

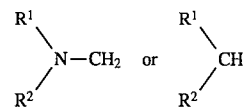

or a pharmaceutically acceptable salt thereof.

The compounds of formula I may exist as geometric and optical isomers and all isomers and mixtures thereof are included herein. Isomers may be separated by means of standard methods such as chromatographic techniques or fractional crystallisation of suitable salts.

The compounds according to the invention may optionally exist as pharmaceutically acceptable acid addition salts or—when the carboxylic acid group is not esterified—as pharmaceutically acceptable metal salts or—optionally alkylated—ammonium salts.

Examples of such salts include inorganic and organic acid addition salts such as hydrochloride, hydrobromide, sulphate, phosphate, acetate, phthalate, fumarate, maleate, citrate, lactate, tartrate, oxalate, or similar pharmaceutically acceptable inorganic or organic acid addition salts, and include the pharmaceutically acceptable salts listed in Journal of Pharmaceutical Science, 66, 2 (1977) which are hereby incorporated by reference.

In a preferred embodiment of the invention within the $R^1$-definition $C_{1-4}$-alkyl is methyl or ethyl and $C_{1-4}$-alkoxy is methoxy or ethoxy and within the $R^2$-substituent $C_{1-8}$-alkyl is methyl, ethyl, propyl, butyl or pentyl and isomers hereof, $C_{1-4}$-alkyl is methyl or ethyl and $C_{1-4}$-alkoxy is methoxy or ethoxy, and X includes methoxy, ethoxy, isopropoxy or n-propoxy, and n includes 1 or 2, and m includes 2 or 3.

The compounds of formula I have a greater lipophilicity—and thus a greater availability to the brain—as well as a far higher affinity to the GABA uptake sites than the parent compounds without the N-substituent (i.e. nipecotic acid and guvacine).

It has been demonstrated that the novel compounds of formula I which inhibit the uptake of GABA from the synaptic cleft possess useful pharmacological properties in the central nervous system, in that they cause a selective enhancement of GABA'ergic activity. Compounds of formula I may be used to treat for example, pain, anxiety, extrapyrimidinal dyskinesia, epilepsy and certain muscular and movement disorders. They are also useful as sedatives, hypnotics and antidepressants.

The compounds of formula I are prepared by the following methods:

Method A:

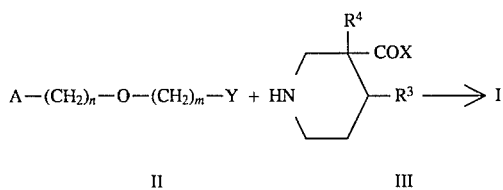

A compound of formula II wherein A, n and m are as defined above and Y is a suitable leaving group such as halogen, p-toluene sulphonate or mesylate may be reacted with an azaheterocyclic compound of formula III wherein $R^3$, $R^4$ and X are as defined above. This alkylation reaction may be carried out in a solvent such as acetone, dibutylether, 2-butanone, tetrahydrofuran, methylisobutylketone, isopropyl acetate or toluene in the presence of a base e.g. potassium carbonate and a catalyst, e.g. an alkali metal iodide at a temperature up to reflux temperature for the solvent used for e.g. 1 to 200 h.

Method B:

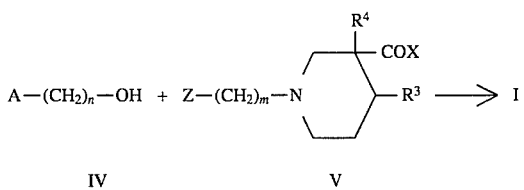

A compound of formula IV wherein A and n are as defined above, may be reacted with a compound of formula V wherein $R^3$, $R^4$, m and X are as defined above and Z is a suitable leaving group such as halogen, p-toluene sulphonate or mesylate. This alkylation reaction may be carried out in a suitable solvent such as dibutylether, 2-butanone, tetrahydrofuran, methylisobutylketone or toluene in the presence of a base e.g. potassium carbonate or sodium hydride at a temperature up to reflux temperature for the solvent used for e.g. 1 to 200 h.

Compounds of formula II, III and IV may readily be prepared by methods familiar to those skilled in the art. Compounds of formula V may be prepared according to the procedure described in EP 374801.

Under certain circumstances it may be necessary to protect the intermediates used in the above methods e.g. a compound of formula III or V with suitable protecting groups. The carboxylic acid group can, for example, be esterified. Introduction and removal of such groups is described in "Protective Groups in Organic Synthesis" T. W. Greene and P. G. M. Wuts, 2ed. (John Wiley, 1991).

Pharmacological Methods

Values for in vitro inhibition of [$^3$H]-GABA uptake for the invention compounds were assessed essentially by the method of Fjalland (Acta Pharmacol. Toxicol. 1978, 42, 73–76).

Male wistar rat cortical tissue was gently homogenized by hand using a glass/PTFE homogenizer in 10 volumes of 0.32M sucrose. Incubation was performed in a 40 mM tris HCl buffer (pH 7.5 at 30° C.) containing 120 nM NaCl, 9.2 nM KCl, 4 mM MgSO$_4$, 2.3 nM CaCl$_2$ and 10 mM glucose, for 60 minutes at 30° C.

Values for inhibition of GABA uptake for some representative compounds are recorded in Table I.

TABLE I

| | Inhibition of [$^3$H]-GABA uptake |
|---|---|
| Example no. | IC$_{50}$ (nM) in vitro |
| 1 | 4500 |
| 2 | 325 |
| 3 | 6400 |
| 4 | 338 |
| 5 | 495 |
| 6 | 2000 |
| 7 | 263 |
| 8 | 150 |
| 9 | 100 |
| 10 | >3000 |
| 11 | 113 |

For the above indications the dosage will vary depending on the compound of formula I employed, on the mode of administration and on the therapy desired. However, in general, satisfactory results are obtained with a dosage of from about 0.5 mg to about 1000 mg, preferably from about 1 mg to about 500 mg of compounds of formula I, conveniently given from 1 to 5 times daily, optionally in sustained release form. Usually, dosage forms suitable for oral administration comprise from about 0.5 mg to about 1000 mg, preferably from about 1 mg to about 500 mg of the compounds of formula I admixed with a pharmaceutical carrier or diluent.

The compounds of formula I may be administered in pharmaceutically acceptable acid addition salt form or where possible as a metal or a lower alkylammonium salt.

This invention also relates to pharmaceutical compositions comprising a compound of formula I or a pharmaceutically acceptable salt thereof and, usually, such compositions also contains a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatin, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

If a solid carrier for oral administration is used, the preparation can be tabletted, placed in a hard gelatin capsule in powder or pellet form or it can be in the form of a troche or lozenge. The amount of solid carrier will vary widely, but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

Generally, the compounds of this invention are dispended in unit dosage form comprising 50–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet, which may be prepared by conventional tabletting techniques contains:

| Core: | |
|---|---|
| Active compound (as free compound or salt thereof) | 100 mg |
| Colloidal silicon dioxide (Aerosil ®) | 1.5 mg |
| Cellulose, microcryst. (Avicel ®) | 70 mg |
| Modified cellulose gum (Ac-Di-Sol ®) | 7.5 mg |
| Magnesium stearate | |
| Coating: | |
| HPMC approx. | 9 mg |
| *Mywacett ® 9–40 T approx. | 0.9 mg |

*Acylated monoglyceride used as plasticizer for film coating.

The route of administration may be any route, which effectively transports the active compound to the appropriate or desired site of action, such as oral or parenteral e.g. rectal, transdermal, subcutaneous, intravenous, intramuscular or intranasal, the oral route being preferred.

EXAMPLES

The process for preparing compounds of formula I is further illustrated in the following examples which however are not to be construed as limiting. Hereinafter, TLC is thin layer chromatography and THF is tetrahydrofuran, $CDCl_3$ is deuterio chloroform and $DMSO-d_6$ is hexadeuterio dimethylsulfoxide. The structures of the compounds are confirmed by either elemental analysis or NMR, where peaks assigned to characteristic protons in the title compounds are presented where appropriate. NMR shifts ($\delta$) are given in parts per million (ppm). M.p. is melting point and is given in °C. Column chromatography was carried out using the technique described by W. C. Still et al, J. Org. Chem. 1978, 43, 2923–2925 on Merck silica gel 60 (Art. 9385). Compounds used as starting materials are either known compounds or compounds which can readily be prepared by methods known per se.

EXAMPLE 1

1-(2-(3-Phenyl-1-propyloxy)ethyl)-3-piperidine-carboxylic acid hydrochloride

Sodium hydride (1.5 g, 37 mmol, 60% oil dispersion) was added portionwise to a stirred solution of 3-phenyl-1-propanol (5.0 g, 37 mmol) in toluene (25 ml) placed under an atmosphere of nitrogen. The mixture was stirred for 30 minutes at ambient temperature and then heated at reflux for 45 minutes. The reaction mixture was allowed to cool and another portion of sodium hydride (1.5 g, 37 mmol, 60% oil dispersion) was added followed by toluene (25 ml). The suspension was heated at reflux for 15 minutes and allowed to cool. Keeping the temperature below 40° C. 1-(2-bromoethyl)-3piperidinecarboxylic acid ethyl ester hydrobromide (12.6 g, 37 mmol, EP 374801) was added portionwise. The reaction mixture was stirred for 3 days and then left for 3 weeks. The mixture was poured into water (200 ml) and extracted with ethyl acetate (100 ml). The phases were separated and the organic phase was extracted with 5% citric acid solution (3×100 ml). The combined acidic phases were extracted with ethyl acetate (100 ml) which was discarded. 4N sodium hydroxide was added to the aqueous phase until pH 8 and then it was extracted with ethyl acetate (2×100 ml). The combined organic extracts were washed with saturated sodium bicarbonate solution and dried ($Na_2SO_4$). The solvent was evaporated in vacuo to give 3.2 g of 1-(2-(3-phenyl-1-propyloxy)ethyl)-3-piperidinecarboxylic acid ethyl ester as an oil.

The above ester (3.2 g, 10 mmol) was dissolved in ethanol (10 ml) and 12N sodium hydroxide (2.5 ml) was added. The mixture was stirred at ambient temperature for 3 h. Excess concentrated hydrochloric acid was added followed by dichloromethane (300 ml). The mixture was dried ($Na_2SO_4$) and the solvent was evaporated in vacuo to give a residue which was re-evaporated twice with acetone. Crystallisation of the residue from a mixture of acetone and ethyl acetate followed by recrystallisation from acetone gave 1.1 g of the title compound as a solid.

M.p. 115°–117° C. Calculated for $C_{17}H_{25}NO_3 \cdot HCl \cdot \frac{1}{2}H_2O$: C, 60.6%; H, 8.1%; N, 4.2%; Found: C, 60.7%; H, 8.1%; N, 3.9%.

EXAMPLE 2

(R)-1-(2-(2-Benzylbenzyloxy)ethyl)-3-piperidine-carboxylic acid hydrochloride

Sodium hydride (2.1 g, 53 mmol, 60% oil dispersion) was added portionwise to a stirred solution of 2-benzylbenzylalcohol (5.0 g, 25 mmol) in dry THF (125 ml) placed under an atmosphere of nitrogen. The mixture was heated at reflux for 1 h and then allowed to cool to ambient temperature within 30 minutes. (R)-1-(2-Bromoethyl)-3-piperidinecarboxylic acid ethyl ester hydrobromide (8.6 g, 25 mmol, EP 374801) was added and the mixture was stirred for 2 days at ambient temperature. The reaction mixture was diluted with THF (100 ml) and filtered. The solvent was evaporated in vacuo to give an oily residue which was purified by column chromatography (700 g, heptane/ethyl acetate=1/1) to give 0.8 g of (R)-1-(2-(2-benzylbenzyloxy)ethyl)-3-piperidinecarboxylic acid ethyl ester as an oil.

The above ester (0.8 g, 2.1 mmol) was dissolved in ethanol (10 ml) and 2N sodium hydroxide (3.1 ml) was added. The mixture was stirred at ambient temperature overnight. Excess concentrated hydrochloric acid was added followed by dichloromethane. The mixture was concentrated in vacuo and water and dichloromethane was added. The phases were separated and the organic phase was dried ($MgSO_4$). The solvent was evaporated in vacuo to give a foamy residue which was re-evaporated with dichloromethane to give 0.65 g of the title compound as an amorphous solid.

$^1$H NMR (DMSO-$d_6$) $\delta$ 3.83 (brs, 2H); 4.03 (s, 2H); 4.53 (s, 2H). Calculated for $C_{22}H_{27}NO_3 \cdot HCl$: C, 67.8%; H, 7.2%; N, 3.6%; Found: C, 68.2%; H, 7.5%; N, 3.4%.

EXAMPLE 3

(R)-1-(2-((1-Phenyl-2-naphthyl)methoxy)ethyl)-3-piperidinecarboxylic acid hydrochloride A 1.0M solution of lithium aluminiumhydride in THF (10 ml, 10 mmol) was placed under an atmosphere of nitrogen and a solution of 1-phenyl-2-naphthalenecarboxylic acid (2.4 g, 10 mmol, Synthesis 1983, 105) in dry THF (10 ml) was added dropwise. When addition was complete the mixture was stirred for 30 minutes at ambient temperature and then 30 minutes at reflux. The reaction mixture was allowed to cool and carefully water (0.4 ml), 4N sodium hydroxide (0.4 ml) and water (1.2 ml) were added successively. The mixture was stirred at ambient temperature for 30 minutes, diluted with diethylether and filtered. The solvent was evaporated in vacuo and the residue was dissolved in toluene. After drying ($MgSO_4$) the solvent was evaporated in vacuo to give 2.3 g of crude (1-phenyl-2-naphthyl)methanol.

The above alcohol (2.3 g) was dissolved in toluene (10 ml) and thionyl bromide (1.0 ml) was added. The mixture was stirred at ambient temperature for 1 h, heated at reflux for 10 minutes and finally stirred at ambient temperature for 30 minutes. The reaction mixture was diluted with toluene (75 ml), washed with a 10% sodium bicarbonate solution and dried ($MgSO_4$). The solvent was evaporated in vacuo to give crude (1-phenyl-2-naphtyl) methylbromide.

Dry ethylene glycol (20 ml) was placed on an ice-bath under an atmosphere of nitrogen and a 2.5M solution of n-butyllithium in hexanes (6.0 ml) was added dropwise. When addition was complete the mixture was stirred for 15 minutes and the above crude bromide dissolved in cyclohexane (5 ml) was added. The reaction mixture was stirred at ambient temperature for 2 days, diluted with water (50 ml) and extracted with diethylether (100 ml). The organic phase was washed with water and dried ($MgSO_4$) and the solvent was evaporated in vacuo. The residue was purified by column chromatography on silica gel (100 g, heptane/ethyl acetate=3/2) to give 2.3 g of 2-((1-phenyl-2-naphthyl)methoxy)ethanol as an oil.

Triethylamine (2.9 ml) was added to a stirred solution of the above alcohol (2.3 g, 8.3 mmol) in dry diethylether (50 ml). A solution of methanesulfonyl chloride (0.96 ml) in dry diethylether (10 ml) was added dropwise. When addition was complete the mixture was stirred for 90 minutes and water (20 ml) was added. The phases were separated and the organic phase was dried. The solvent was evaporated in vacuo to give the crude mesylate which was dissolved in acetone (50 ml). (R)-3-Piperidinecarboxylic acid ethyl ester tartrate (3.8 g, 12.4 mmol) and potassium carbonate (2.9 g, 21 mmol) were added and the reaction mixture was heated at reflux for 4 days. The cooled mixture was filtered and the solvent was evaporated in vacuo to give a residue which was purified by column chromatography on silica gel (150 g, heptane/ethyl acetate=1/1). This afforded 3.0 g of (R)-1-(2-((1-phenyl-2-naphthyl)methoxy)ethyl)-3-piperidinecarboxylic acid ethyl ester as an oil.

The above ester (3.0 g, 7.2 mmol) was dissolved in ethanol (20 ml) and 4N sodium hydroxide (5.4 ml) was added. The mixture was stirred at ambient temperature for 3 h. Concentrated hydrochloric acid (2.4 ml) was added followed by dichloromethane (300 ml) and the phases were separated. The organic phase was washed with water (20 ml), dried ($MgSO_4$) and the solvent evaporated in vacuo. The residue was re-evaporated with acetone to give 2.5 g of the title compound as a solid.

M.p. 153°–155° C. Calculated for $C_{25}H_{27}NO_3 \cdot HCl$: C, 70.5%; H, 6.6%; N, 3.3%; Found: C, 70.1%; H, 6.7%; N, 3.1%.

EXAMPLE 4

(R)-1-(2-(2-Phenylbenzyloxy)ethyl)-3-piperidinecarboxylic acid hydrochloride

To a mixture of lithium aluminiumhydride (1.0 g, 25 mmol) in dry THF (25 ml) placed under an atmosphere of nitrogen 2-biphenylcarboxylic acid (5.0 g, 25 mmol) was added portionwise. When addition was complete the mixture was stirred for 30 minutes at ambient temperature and then 30 minutes at reflux. The reaction mixture was allowed to cool and carefully water (1.0 ml), 4N sodium hydroxide (1.0 ml) and water (3.0 ml) were added successively. The mixture was diluted with diethylether (50 ml) and the phases were separated. The organic phase was dried ($MgSO_4$), the solvent evaporated in vacuo and the residue re-evaporated with toluene. To the oily residue thionyl chloride (5 ml) was carefully added and the mixture was stirred at ambient temperature for 1 h. Excess thionyl chloride was removed in vacuo to give a residue which was dissolved in toluene. The organic solution was washed with 10% sodium bicarbonate and dried. The solvent was evaporated in vacuo to give 4.0 g of crude 2-biphenylmethylchloride.

A 2.5M solution of n-butyllithium in hexanes (10 ml) was added dropwise to dry ethylene glycol (20 ml) placed on an ice-bath under an atmosphere of nitrogen. When addition was complete the mixture was stirred for 30 minutes and the above crude chloride was added. The reaction mixture was stirred at ambient temperature for 4 days, diluted with water (100 ml) and extracted with diethylether. The organic phase was washed with water and dried ($MgSO_4$) and the solvent evaporated in vacuo. The residue was purified by column chromatography on silica gel (200 g, heptane/ethyl acetate= 3/2) to give 2.2 g of 2-(2-phenylbenzyloxy)ethanol as an oil.

A solution of the above alcohol (2.2 g, 10 mmol) in dry THF (20 ml) was placed on an ice-bath under an atmosphere of nitrogen. A 2.5M solution of n-butyllithium in hexanes (4.0 ml, 10 mmol) was added dropwise and when addition was complete the mixture was stirred for 15 minutes. Methanesulfonyl chloride (1.1 g, 10 mmol) was added, the ice-bath was removed and the mixture was stirred at ambient temperature for 2 h. The volatiles were evaporated in vacuo and acetone (50 ml), (R)-3-piperidinecarboxylic acid ethyl ester tartrate (4.6 g, 15 mmol) and potassium carbonate (3.5 g, 25 mmol) were added. The mixture was heated at reflux for 6 days, cooled and filtered. The solvent was evaporated in vacuo to give a residue which was purified by column chromatography on silica gel (200 g, heptane/ethyl acetate= 3/2). This afforded 1.9 g of (R)-1-(2-(2-phenylbenzyloxy)ethyl)-3-piperidinecarboxylic acid ethyl ester as an oil.

The above ester (1.9 g, 5.2 mmol) was dissolved in ethanol (15 ml) and 4N sodium hydroxide (3.9 ml) was added. The mixture was stirred at ambient temperature for 2 h. Concentrated hydrochloric acid (2 ml) was added followed by dichloromethane (250 ml) and the phases were separated. The organic phase was washed with water (5 ml), dried ($MgSO_4$) and the solvent evaporated in vacuo. The residue was re-evaporated with acetone and then crystallised from acetone to give 1.3 g of the title compound as a solid.

M.p. 148°–149° C. Calculated for $C_{21}H_{25}NO_3 \cdot HCl$: C, 67.1%; H, 7.0%; N, 3.7%; Found: C, 67.2%; H, 7.0%; N, 3.4%.

EXAMPLE 5

E-(R)-1-(2-((2,3-Diphenyl-2-propen-1-yl)oxy)ethyl)-3-piperidinecarboxylic acid hydrochloride A mixture of 1,2-diphenyl-1-propene (9.7 g, 50 mmol), N-bromosuccinimide (8.9 g, 50 mmol), dibenzoylperoxide (0.1 g) and tetrachloromethane (50 ml) was heated at reflux for 21 h. The mixture was filtered cold and the solvent evaporated from the filtrate in vacuo to give 13.1 g of 3-bromo-1,2-diphenyl-1-propene as an E/Z isomeric mixture.

Ethylene glycol (40 ml) under an inert atmosphere was cooled on an icebath and a 2.5M solution of n-butyllithium in hexane (23 ml, 58 mmol) was carefully added. After stirring for 20 min at room temperature the above bromide dissolved in a small portion of cyclohexane was added. After removing the hexanes by passing nitrogen over the reaction mixture stirring was continued for 5 h. Water (75 ml) was added and the mixture was extracted with ethyl acetate (3×75 ml). The combined organic phases were washed with water (25 ml) and dried ($Na_2SO_4$). The solvent was evaporated in vacuo and the residue was purified by column chromatography on silica gel (300 g, n-heptane/ethyl acetate=7/3) to give 6.2 g of Z-2-((2,3-diphenyl-2-propen-1-yl)oxy)ethanol and 2.7 g of E-2-((2,3-diphenyl-2-propen-1-yl)oxy)ethanol.

To a solution of the above E-alcohol (2.5 g, 10 mmol) in anhydrous tetrahydrofuran was added a 2.5M solution of n-butyllithium in hexane (4.0 ml, 10 mmol) at 0° C. The mixture was stirred at 0° C. for 10 min and 4-methylbenzenesulfonyl chloride (1.9 g, 10 mmol) was added and the mixture was stirred at ambient temperature for 1 h. After the solvent was evaporated in vacuo the residue was dissolved in acetone (25 ml) and (R)-3-piperidinecarboxylic acid ethyl ester (2.4 g, 15 mmol) and potassium carbonate (2.5 g, 18 mmol) were added. The mixture was stirred at room temperature for 7 days, filtered and the solvent was evaporated from the filtrate in vacuo. The residue was dissolved in toluene (30 ml) and the solution was extracted with 1N hydrochloric acid. The aqueous phase was washed with ethyl acetate (10 ml), pH adjusted to 10 with solid potassium carbonate and extracted with ethyl acetate (3×50 ml). The combined ethyl acetate phases were dried ($Na_2SO_4$) and the solvent was evaporated in vacuo to give 1.0 g of crude ester. The toluene phase was neutralised with 10% potassium carbonate and the organic phase dried ($Na_2SO_4$). The solvent was evaporated in vacuo to give an additional 4.3 g of crude ester. The combined crude products were purified by column chromatography on silica gel (150 g, n-heptane/ethyl acetate=1/1) to give 1.45 g E-(R)-1-(2-((2,3-diphenyl-2-propen-1-yl)oxy)ethyl)-3-piperidinecarboxylic acid ethyl ester.

The above ester (1.45 g, 3.7 mmol) was dissolved in absolute ethanol (15 ml) and 4N sodium hydroxide (1.9 ml) was added. After stirring at ambient temperature for 4 h the mixture was diluted with dichloromethane (300 ml), cooled to 0° C. and 4N hydrochloric acid (4 ml) was added. The mixture was dried ($Na_2SO_4$) and the solvent evaporated in vacuo. The residue was re-evaporated with acetone, suspended in acetone (10 ml), the precipitate collected and dried in the air. This afforded 1.2 g of the title compound as a solid.

M.p. 214°–215° C. Calculated for $C_{23}H_{27}NO_3$.HCl C, 68.7%; H, 7.0%; N, 3.5%; Found C, 68.7%; H, 7.3%; N, 3.6%.

$^1$H-NMR (DMSO-$d_6$) δ 4.36 (s,2H); 6.73 (s, 1H).

EXAMPLE 6

Z-(R)-1-(2-((2,3-Diphenyl-2-propen-1-yl)oxy)ethyl)-3-piperidinecarboxylic acid hydrochloride To a solution of Z-2-((2,3-diphenyl-2-propen-1-yl)oxy)ethanol (6.0 g, 24 mmol, prepared according to example 5) under an inert atmosphere in anhydrous THF was dropwise added a 2.5M solution of n-butyllithium in hexane (10.0 ml, 24 mmol) at 0° C. The mixture was stirred at 0° C. for 10 min, then 4-methylbenzenesulfonyl chloride (4.5 g, 24 mmol) was added and stirring was continued at ambient temperature for 1 h. The solvent was evaporated in vacuo, the residue was dissolved in acetone (50 ml) and (R)-3-piperidinecarboxylic acid ethyl ester (5.6 g, 35 mmol) and potassium carbonate (5.9 g, 43 mmol) were added. The mixture was stirred at room temperature for 7 days, filtered and the solvent was evaporated from the filtrate in vacuo. The residue was dissolved in toluene (70 ml) and the solution was extracted with 1N hydrochloric acid (70 ml). The aqueous phase was washed with ethyl acetate (20 ml), pH adjusted to 10 with solid potassiumcarbonate and extracted with ethyl acetate (3×100 ml). The organic phases were dried ($Na_2SO_4$) and the solvent was evaporated in vacuo to give 3.2 g of crude ester. The toluene phase was neutralised with 10% potassium carbonate and the organic phase dried ($Na_2SO_4$). The solvent was evaporated in vacuo to give an additional 12.3 g of crude ester. The combined crude products were purified by column chromatography on silica gel (300 g, n-heptane/ethyl acetate=1/1) to give 5.7 g Z-(R)-1-(2-((2,3-diphenyl-2-propen-1-yl)oxy)ethyl)-3-piperidinecarboxylic acid ethyl ester.

The above ester (3.15 g, 8 mmol) was dissolved in absolute ethanol (25 ml) and 4N sodium hydroxide (4.0 ml) was added. After stirring at ambient temperature for 4.5 h the mixture was diluted with dichloromethane (400 ml), cooled to 0° C. and 4N hydrochloric acid (7.5 ml) was added. The mixture was dried ($Na_2SO_4$) and the solvent evaporated in vacuo. The residue was re-evaporated with acetone, suspended in diethylether and stirred for 21 days to give an amorphous solid which was triturated 16 h with anhydrous diethylether. This afforded 2.1 g of the title compound as an amorphous solid.

Calculated for $C_{23}H_{27}NO_3$.HCl C, 68.7%; H, 7.0%; N, 3.5%; Found: C, 68.1%; H, 7.1%; N, 3.6%.

$^1$H-NMR (DMSO-$d_6$) δ 4.52 (s,2H); 7.23 (s, 1H).

EXAMPLE 7

(R)-1-(2-(2-(N-(2-Methyl-1-propyl)-N-phenylamino)ethoxy)ethyl)-3-piperidinecarboxylic acid hydrochloride A mixture of N-(2-methyl-1-propyl)-N-phenylamine (14.9 g, 100 mmol), chloroacetic anhydride (19.0 g, 111 mmol) and water (100 ml) was heated at 70° C. for 1 h. The reaction mixture was poured into iced water (300 ml) and pH in the aqueous phase was adjusted to 2 with concentrated hydrochloric acid. The precipitated compound was collected and dried in vacuo to give 11.3 g of 2-chloro-N-(2-methyl-1-propyl)-N-phenylacetamide.

To a solution of ethylene glycol (12.4 g, 200 mmol) in DMF (50 ml) was carefully added potassium tert-butoxide (16.8 g, 150 mmol) while the temperature was kept below 70° C. The resulting mixture was stirred at ambient temperature for 30 min, then a solution of the above acetamide (11.3 g, 50 mmol) in DMF (5 ml) was added in one portion and the mixture was stirred at room temperature for 1.5 h. The reaction mixture was poured into iced water (400 ml) and extracted with dichloromethane (2×50 ml). The combined organic phases were dried ($MgSO_4$) and the solvent was evaporated in vacuo to give 12.5 g of 2-(2-hydroxyethoxy)-N-(2-methyl-1-propyl)-N-phenylacetamide.

To a suspension of lithium aluminium hydride (2.8 g, 75 mmol) in anhydrous toluene (16 ml) was added dropwise anhydrous THF (20 ml). A solution of the above hydroxyethylacetamide (12.5 g, 50 mmol) in anhydrous toluene (5 ml) was added dropwise while the temperature was kept below 75° C. When addition was complete the mixture was stirred at room temperature for 1 h. Water (10 ml) was carefully added and when the initial exotherm had subsided potassium carbonate (10 g) was added in one portion. The mixture was stirred for 15 min. and then filtered. The filterpad was washed with dichloromethane (2×100 ml) and the phases in the filtrate separated. The organic phase was dried (MgSO$_4$) and the solvent evaporated in vacuo to give 10.6 g of 2-(2-(N-(2-methyl-1-propyl)-N-phenylamino)ethoxy)ethanol.

A mixture of the above alcohol (10.6 g, 45 mmol), triethylamine (7.3 ml, 53 mmol) and dichloromethane (100 ml) was cooled to −10° C. and methanesulfonyl chloride (3.3 ml, 42 mmol) was added dropwise while the temperature was kept below −5° C. When addition was complete the mixture was stirred at 0° C. for 1 h and then at room temperature for 30 min. The reaction mixture was washed with 0.1N hydrochloric acid (2×50 ml), water (50 ml) and brine (10 ml). The organic phase was dried (MgSO$_4$) and the solvent was evaporated in vacuo to give 13.4 g of 2-(2-(N-(2-methyl-1-propyl)-N-phenylamino)ethoxy)ethyl methanesulfonate.

A mixture of the above methanesulfonate (13.4 g, 43 mmol), (R)-3-piperidinecarboxylic acid ethyl ester (10.0 g, 64 mmol), lithium carbonate (3.1 g, 43 mmol) and isopropyl acetate (100 ml) was stirred at ambient temperature for 16 h and then at reflux for 24 h. The reaction mixture was filtered and the solvent was evaporated from the filtrate in vacuo. The residue was dissolved in dichloromethane (100 ml), dried (MgSO$_4$) and purified by column chromatography on silica gel (100 g, n-heptane/ethyl acetate=4/1) to give 8.0 g of (R)-1-(2-(2-(N-(2-methyl-1-propyl)-N-phenylamino)ethoxy)ethyl)-3-piperidinecarboxylic acid ethyl ester.

To a solution of the above ester (8.0 g, 21 mmol) in anhydrous toluene (30 ml) was added a solution of chlorotrimethylsilane (4.6 g, 42 mmol) in anhydrous toluene (10 ml). Methanol (1.7 ml, 42 mmol) was carefully added and the resulting mixture left for crystallisation to give 6.2 g of (R)-1-(2-(2-(N-(2-methyl-1-propyl)-N-phenylamino)ethoxy)ethyl)-3-piperidinecarboxylic acid ethyl ester dihydrochloride.

The above ester dihydrochloride was suspended in water (20 ml) and pH in the aqueous phase adjusted to 14 with 9N sodium hydroxide. The mixture was heated at reflux for 30 min, then cooled to ambient temperature and pH adjusted to 0 with concentrated hydrochloric acid. The aqueous phase was washed with n-heptane (50 ml) and then concentrated in vacuo. The residue was extracted with dichloromethane (2×50 ml) and the solvent evaporated in vacuo. This afforded 1.2 g of the title compound as a foam.

$^1$H NMR (DMSO-d$_6$) δ 3.75 (m,4H).

EXAMPLE 8

(R)-1-(2-(2-(N-(2-Chloro-4-fluorophenyl)-N-(2-methyl-1-propyl)amino)-ethoxy)ethyl)-3-piperidinecarboxylic acid hydrochloride A mixture of N-(2-chloro-4-fluorophenyl)acetamide (25.0 g, 133 mmol), concentrated hydrochloric acid (25 ml) and ethanol(50 ml) was heated at reflux for 3 h. The mixture was cooled to 0° C. and left for crystallisation. The precipitate was collected and dried in vacuo to give 20.0 g of 2-chloro-4-fluorophenylammonium chloride.

The above ammonium chloride (20.0 g, 11 mmol) was dissolved in water (250 ml) and pH in the aqueous phase was adjusted to 7.5 with 9N sodium hydroxide and 2-methylpropionic anhydride was added. The mixture was heated at reflux for 45 min. and then cooled on an icebath. The precipitated product was collected and recrystallised from ethanol/water 1/1 to give 21.0 g of N-(2-chloro-4-fluorophenyl)-2-methylpropanamide.

A suspension of the above propanamide (19.9 g, 92 mmol) in THF (200 ml) was cooled on an icebath. A 1M solution of borane in THF (100 ml, 100 mmol) was added and the mixture stirred at room temperature for 16 h. Methanol (50 ml) was carefully added followed by 1N hydrochloric acid (50 ml). The volume was concentrated in vacuo to 50 ml, water (200 ml) was added and pH in the aqueous phase was adjusted to 10 with 2N sodium hydroxide. The mixture was extracted with dichloromethane (3×100 ml) and the combined organic phases were extracted with 4N hydrochloric acid. The phases were separated, pH in the aqueous phase was adjusted to 10 with 6N sodium hydroxide and extracted with dichloromethane (2×100 ml). The organic phase was washed with water (50 ml) and dried (MgSO$_4$). The solvent was evaporated in vacuo to give 15.0 g of N-(2-chloro-4-fluorophenyl)-N-(2-methyl-1-propyl)amine.

A solution of the above amine (15.0 g, 74 mmol) and triethylamine (12.0 g, 119 mmol) in dichloromethane (200 ml) was cooled to −10° C. and chloroacetyl chloride (11.3 g, 113 mmol) was carefully added while the temperature was kept below 10° C. The mixture was then stirred at ambient temperature for 1 h. The reaction mixture was poured into water (200 ml) and extracted with dichloromethane (2×100 ml). The organic phase was washed with 4N hydrochloric acid (2×50 ml), water (100 ml) and saturated aqueous sodium hydrogencarbonate (50 ml) and dried (MgSO$_4$). The solvent was evaporated in vacuo to give 13.6 g of 2-chloro-N-(2-chloro-4-fluorophenyl)-N-(2-methyl-1-propyl)acetamide.

A mixture of potassium tert-butoxide (11.6 g, 104 mmol) and ethylene glycol (140 ml) was stirred for 0.5 h, and the above amide (13.6 g, 52 mmol) was then added and the mixture was heated at 90° C. for 2 h. Water (100 ml) was added and the resulting mixture extracted with ethyl acetate (3×100 ml). The combined organic phases were washed with water (3×50 ml) and brine (10 ml) and dried (MgSO$_4$). The solvent was evaporated in vacuo to give 17.4 g of N-(2-chloro-4-fluorophenyl)-N-(2-methyl-1-propyl)-2-(2-hydroxyethoxy)acetamide.

A solution of the above acylamide (17.2 g, 57 mmol) in anhydrous THF (150 ml) was cooled to −5° C. under an inert atmosphere and sodium borohydride (1.63 g, 43 mmol) was added and the resulting mixture was stirred for 5 min. Then borontrifluoride diethyletherate (8.1 g, 57 mmol) was carefully added while the temperature was kept below 0° C. The mixture was stirred at 0° C. for 1 h, then at room temperature for 16 h and finally heated at 50° C. for 1 h. Sodium borohydride (1.63 g, 43 mmol) was added at room temperature and borontrifluoride diethyletherate (7.08 ml, 63 mmol) was carefully added while the temperature was kept below 30° C. The mixture was stirred at room temperature for 1 h and heated to 50° C. for 30 min. Methanol (20 ml), water (20 ml) and ethyl acetate (100 ml) were added and the phases were separated. The aqueous phase was extracted with ethyl acetate (2×50 ml) and the combined organic phases were dried (MgSO$_4$). The solvent was evaporated in vacuo and the residue purified by column chromatography on silica gel (150 g, n-heptane/ethyl acetate gradient 9/1 to 1/1) to give 10.0 g of 2-(2-(N-(2-chloro-4-fluorophenyl)-N-(2-methyl-1-propyl)amino)ethoxy)ethanol.

A mixture of the above alcohol (9.7 g, 34 mmol), triethylamine (5.6 ml, 41 mmol) and dichloromethane (100 ml) was cooled to −30° C. and a solution of methanesulfonyl chloride (4.2 g, 37 mmol) in anhydrous dichloromethane (10 ml) was added dropwise while the temperature was kept below −15° C. When addition was complete the mixture was allowed to warm to room temperature and water (50 ml) was added. The organic phase was washed with water (50 ml), 0.2N hydrochloric acid (2×25 ml), water (2×25 ml) and brine (10 ml) and dried (MgSO$_4$). The solvent was evaporated in vacuo to give 12.5 g of 2-(2-(N-(2-chloro-4-fluorophenyl)-N-(2-methyl-1-propyl)amino)ethoxy)ethyl methanesulfonate.

A mixture of the above methanesulfonate (12.5 g, 34 mmol), (R)-3-piperidinecarboxylic acid ethyl ester (+)-tartrate (13.8 g, 45 mmol), lithium carbonate (10.0 g, 135 mmol) and isopropyl acetate (150 ml) was heated at reflux for 4 days. The reaction mixture was filtered and the filterpad was washed with ethyl acetate. The combined organic phases were washed with water (50 ml) and saturated aqueous ammonium chloride (50 ml). The solvent was evaporated in vacuo to give 13.1 g of (R)-1-(2-(2-(N-(2-chloro-4-fluorophenyl)-N-(2-methyl-1-propyl)amino)ethoxy)ethyl)-3-piperidinecarboxylic acid ethyl ester.

The above ester (13.1 g, 31 mmol) was dissolved in ethanol (50 ml), 2N sodium hydroxide (50 ml) was added and the mixture was heated at reflux for 1 h. After cooling to ambient temperature pH was adjusted to 0 with concentrated hydrochloric acid. The resulting mixture was washed with dichloromethane (2×100 ml) and pH in the aqueous phase was adjusted to 2.5 with 1N sodium hydroxide. The mixture was extracted with dichloromethane (100 ml) and the solvent was evaporated from the organic phase in vacuo. To the residue was added acetone (50 ml) and diethylether (50 ml) and the mixture was left for crystallisation. This afforded 5.8 g of the title compound.

$^{-1}$H NMR (DMSO-d$_6$) δ 3.75 (2H,dd).

EXAMPLE 9

(R)-1-(2-(2-(2-Benzylphenyl)ethoxy)ethyl)-3-piperidinecarboxylic acid hydrochloride To a solution of 2-benzylphenylacetic acid (5.5 g, 24 mmol, J. Am. Chem. Soc. 1955, 77, 5078) in THF (100 ml) a solution of lithium aluminiumhydride in THF (24 ml, 24 mmol, 1M) was added dropwise on an ice-bath. When addition was complete the mixture was stirred for 1 h at ambient temperature. Water (1 ml), 4N sodium hydroxide (2 ml) and water (4 ml) were added successively. The mixture was filtered and the filtrate was diluted with diethylether (250 ml). The phases were separated and the organic phase was washed with saturated ammonium chloride solution (3×100 ml) and dried (MgSO$_4$). The solvent was evaporated in vacuo to give 4.8 g of crude 2-(2-benzylphenyl)ethanol as an oil.

To a mixture of the alcohol prepared above (4.8 g, 23 mmol), 2-bromoethyl tetrahydro-2-pyranylether (9.6 g, 46 mmol) and dimethylsulfoxide (100 ml), potassium hydroxide (2.6 g, 46 mmol) was added. The reaction mixture was stirred at ambient temperature for 20 h and then heated at 100° C. for 3 h. The reaction mixture was allowed to cool, poured into icewater (200 ml) and extracted with diethylether (2×150 ml). The combined organic extracts were dried (MgSO$_4$) and the solvent was evaporated in vacuo to give 4.6 g of an oily residue. This oil was submitted to column chromatography on silica gel (3×40 cm) using a mixture of heptane and ethyl acetate (1/4) as eluent. This afforded 1.3 g of 2-(2-(2-benzylphenyl)ethoxy)ethanol as an oil.

The above alcohol (1.3 g, 6.1 mmol) was dissolved in dichloromethane (50 ml) and triethylamine (10 ml) was added. Methanesulfonyl chloride (0.77 g, 6.7 mmol) was added dropwise at ambient temperature. When addition was complete the reaction mixture was diluted with dichloromethane (100 ml), washed with water (3×50 ml) and dried (MgSO$_4$). The solvent was evaporated in vacuo to give a residue which was dissolved in acetone (100 ml). To this solution (R)-3-piperidinecarboxylic acid ethyl ester tartrate (2.8 g, 9.5 mmol) and potassium carbonate (2.1 g, 15.3 mmol) were added and the mixture was heated at reflux for 72 h. An additional portion of (R)-3-piperidinecarboxylic acid ethyl ester tartrate (1.4 g, 4.8 mmol) was added and heating was continued for another 24 h. The mixture was allowed to cool and was filtered. The solvent was evaporated in vacuo to give a residue which was submitted to column chromatography on silica gel (3×30 cm) using a gradient of heptane and ethyl acetate (1/1–3/7) as eluent. This afforded 0.9 g of (R)-1-(2-(2-(2-benzylphenyl)ethoxy)ethyl)-3-piperidinecarboxylic acid ethyl ester as an oil.

The above ester (0.8 g, 2 mmol) was dissolved in ethanol (10 ml) and 2N sodium hydroxide (2 ml) was added. The mixture was stirred at ambient temperature for 20 h and ethanol was evaporated in vacuo. The residue was diluted with water (5 ml) and washed with diethylether. Concentrated hydrochloric acid was added to the alkaline aqueous phase until strong acidic reaction. The resulting mixture was extracted with dichloromethane (3×100 ml) and the combined organic extracts were dried (MgSO$_4$). The solvent was evaporated in vacuo to give a foamy residue which was crystallised from acetone. This afforded 0.52 g of the title compound as a solid.

M.p. 144°–145° C. Calculated for C$_{23}$H$_{29}$NO$_3$.HCl: C, 68.4%; H, 7.5%; N, 3.5%; Found: C, 68.1%; H, 7.7%; N, 3.1%.

EXAMPLE 10

(R)-1-(2-(3-Benzylbenzyloxy)ethyl)-3-piperidinecarboxylic acid hydrochloride

To a suspension of 3-benzylbenzoic acid (15 g, 70 mmol) in THF (100 ml) a solution of lithium aluminiumhydride in THF (80 ml, 80 mmol, 1M) was added dropwise. When addition was complete the mixture was stirred for 30 minutes at ambient temperature and then heated at reflux for 40 minutes. The reaction mixture was allowed to cool and water (3 ml), diethyl ether (100 ml), 4N sodium hydroxide (6 ml) and water (12 ml) were added successively. The mixture was stirred for 30 minutes, filtered and the solvent evaporated in vacuo. The residue was dissolved in toluene (200 ml) and dried (MgSO$_4$) overnight. The solvent was evaporated in vacuo to give 11.9 g of crude 3-benzylbenzylalcohol as an oil.

To the above alcohol (11.9 g, 60 mmol) in toluene (50 ml) thionylbromide (16.2 g, 80 mmol) was added dropwise. When addition was complete the mixture was stirred at ambient temperature for 1 h and then heated at reflux for 15 minutes. The reaction mixture was allowed to cool to ambient temperature and then diluted with toluene (400 ml). The resulting mixture was washed with 5% sodium bicarbonate (2×150 ml), water (150 ml) and dried (MgSO$_4$). The solvent was evaporated in vacuo to give 15.3 g of an oily residue containing 3-benzylbenzylbromide. A 2.5M solution of n-butyllithium in hexanes (36 ml) was added dropwise to dry ethylene glycol (120 ml) placed on an ice-bath under an atmosphere of nitrogen. When addition was complete the mixture was stirred for 30 minutes and the above benzylbromide was added in one portion followed by cyclohexane (30 ml) for rinsing and the reaction mixture was stirred at ambient temperature for 72 h. Water (200 ml) was added and the resulting mixture was extracted with diethylether (2×150 ml). The combined organic extracts were dried (MgSO$_4$) and the solvent was evaporated in vacuo to give a residue which was submitted to column chromatography on silica gel (600 ml) using a mixture of heptane and ethyl acetate (3/2) as eluent. This afforded 8.0 g of 2-(3-benzylbenzyloxy)ethanol.

The above alcohol (5.0 g, 21 mmol) was dissolved in dry diethylether (100 ml) and triethylamine (7.3 ml) was added. Methanesulfonyl chloride (3.5 g, 31 mmol) dissolved in dry diethylether (20 ml) was added dropwise at ambient temperature. When addition was complete the reaction mixture was left overnight. Water (50 ml) was added and the mixture was stirred for 10 minutes. The phases were separated, the organic phase was dried (MgSO$_4$) and the solvent was evaporated in vacuo to give a residue which was dissolved in acetone (150 ml). To this solution (R)-3-piperidinecarboxylic acid ethyl ester tartrate (9.5 g, 31 mmol) and potassium carbonate (7.3 g, 53 mmol) were added and the mixture was heated at reflux for 96 h. The mixture was allowed to cool, diluted with acetone (150 ml) and filtered. The solvent was evaporated in vacuo to give a residue which was submitted to column chromatography on silica gel (500 ml) using a mixture of heptane and ethyl acetate (1/1) as eluent. This afforded 4.3 g of (R)-1-(2-(3-benzylbenzyloxy)ethyl)-3-piperidinecarboxylic acid ethyl ester as an oil.

The above ester (4.2 g, 11 mmol) was dissolved in ethanol (20 ml) and 2N sodium hydroxide (16.3 ml) was added. The mixture was stirred at ambient temperature for 16 h and ethanol was evaporated in vacuo. The residue was diluted with water (20 ml) and concentrated hydrochloric acid was added until acidic reaction (pH 2). The resulting mixture was extracted with dichloromethane (2×100 ml) and the combined organic extracts were dried (MgSO$_4$). The solvent was evaporated in vacuo to give a foamy residue which was crystallised from acetone. This afforded 2.7 g of the title compound as a solid.

M.p. 135°–137° C. Calculated for C$_{22}$H$_{27}$NO$_3$.HCl: C, 67.8%; H, 7.2%; N, 3.6%; Found: C, 68.0%; H, 7.4%; N, 3.3%.

EXAMPLE 11

(R)-1-(2-(2-(Biphenyl-2-yl)ethoxy)ethyl)-3-piperidinecarboxylic acid hydrochloride.

2-Bromobiphenyl (20.0 g, 86 mmol) in THF (85 ml) was dropwise added to a refluxing suspension of magnesium (2.1 g, 86 mmol) in THF (15 ml). The reaction mixture was refluxed for 18 h and an extra batch of 2-bromobiphenyl (2.0 g, 8.6 mmol) was added. The reaction mixture was refluxed for 2 h and cooled to 0° C. on an icebath. Ethyleneoxide (14.0 g, 0.32 mol) was was added. The reaction mixture was refluxed for 18 h, cooled to 0° C. and a saturated solution of ammonium chloride (100 ml) was dropwise added at this temperature. The reaction mixture was diluted with diethyl ether (100 ml) and concentrated hydrochloric acid was added until pH 2. The organic phase was separated, dried (MgSO$_4$) and concentrated in vacuo. The residue was submitted to column chromatography on silica gel (800 ml) using heptane and ethyl acetate (7:3) as eluent to give 8.5 g of 2-(biphenyl-2-yl)ethanol as an oil.

A mixture of the alcohol prepared above (8.5 g, 43 mmol), 2-bromoethyltetrahydro-2-pyranylether (17.9 g, 86 mmol) and potassium hydroxide (9.6 g, 171 mmol) in dimethylsulfoxide (100 ml) was stirred at ambient temperature for 72 h. An extra batch of 2-bromoethyltetrahydro-2-pyranylether (3.6 g, 17 mmol) was added and the mixture stirred for 48 h at ambient temperature. Water (350 ml) was added and the mixture was extracted with diethylether (2×250 ml). The organic phases were combined, washed with water (100 ml), dried (MgSO$_4$) and concentrated in vacuo. The residue was submitted to column chromatography on silica gel (400 ml) using heptane and ethyl acetate (3:2) as eluent to give 6.6 g of 2-(2-(biphenyl-2-yl)ethoxy)ethanol as an oil.

Methanesulfonyl chloride (4.7 g, 41 mmol) in dry diethylether (20 ml) was dropwise added to a solution of the alcohol prepared above (6.6 g, 27 mmol) and triethylamine (6.9 g, 67 mmol) in dry diethylether (80 ml). The reaction mixture was stirred at ambient temperature for 3 h and diluted with diethylether (50 ml). Water (100 ml) was added and the organic phase was washed with water (50 ml), dried (MgSO$_4$) and concentrated in vacuo. The residue was dissolved in acetone (150 ml) and (R)-3-piperidinecarboxylic acid ethyl ester tartrate (12.6 g, 41 mmol) was added together with potassium carbonate (9.4 g, 68 mmol). The reaction mixture was refluxed for 6 days, diluted with acetone (100 ml), filtered and concentrated in vacuo. The residue was submitted to column chromatography on silica gel (500 ml) using heptane and ethyl acetate (1:3) as eluent to give 6.0 g of (R)-1-(2-(2-(biphenyl-2-yl)ethoxy)ethyl)-3-piperidinecarboxylic acid ethyl ester as an oil.

The above ester (6.0 g, 16 mmol) was dissolved in ethanol (30 ml) and 2N sodium hydroxide (1.3 ml) was added. The mixture was stirred at ambient temperature for 18 h and the ethanol was removed in vacuo. The residue was adjusted to pH 2 with concentrated hydrochloric acid (6 ml) and extracted with dichloromethane (2×150 ml). The organic phases were combined, dried (MgSO$_4$) and concentrated in vacuo. The residue was crystallised from acetone (30 ml) to give 4.7 g of the title compound as a white solid.

M.p. 122°–124° C. Calculated for C$_{22}$H$_{27}$N$_1$O$_3$.HCl: C, 67.8%; H, 7.2%; N, 3.6% Found: C, 67.9%; H, 7.3%; N, 3.5%

We claim:
1. A compound of formula I

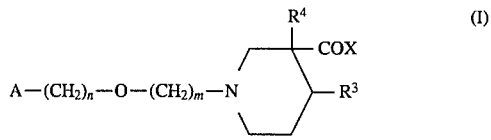

wherein

R$^3$ and R$^4$ each represents hydrogen or may together represent a bond;

X is hydroxy or C$_{1-4}$-alkoxy;

n is 0, 1 or 2;

m is 2, 3 or 4; and

A is

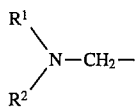

wherein

R¹ is a saturated or unsaturated five or six-membered carbocyclic ring optionally substituted with one or two halogen(s), straight or branched $C_{1-4}$-alkyl, phenyl, $C_{1-4}$-alkyl substituted with phenyl or $C_{2-4}$-alkenyl substituted with phenyl wherein the phenyl groups may be optionally substituted with halogen, $C_{1-4}$-alkyl, $C_{1-4}$-alkoxy or trifluoromethyl, and wherein the saturated or unsaturated five or six-membered carbocyclic ring is optionally fused with a benzo ring; and R² is hydrogen, straight or branched $C_{1-8}$-alkyl, or straight or branched $C_{2-8}$-alkenyl; or a pharmaceutically acceptable salt thereof.

2. A compound according to claim 1, wherein the carbocyclic ring is substituted with phenyl which is optionally substituted with halogen, $C_{1-4}$-alkyl, $C_{1-4}$-alkoxy or trifluoromethyl.

3. A compound according to claim 1, wherein the carbocyclic ring is fused with a benzo ring.

4. A compound according to claim 1 which is (R)-1-(2-(2-(N-(2-Methyl-1-propyl)-N-phenylamino)ethoxy)ethyl)-3-piperidinecarboxylic acid or a pharmaceutically acceptable salt thereof.

5. A compound according to claim 1 which is (R)-1-(2-(2-(N-(2-Chloro-4-fluorophenyl)-N-(2-methyl-1-propyl)amino)ethoxy)ethyl)-3-piperidinecarboxylic acid or a pharmaceutically acceptable salt thereof.

6. A pharmaceutical composition comprising a compound according to claim 1 together with a pharmaceutically acceptable carrier or diluent.

7. The pharmaceutical composition according to claim 6, wherein the compound is present in an amount between 0.5 mg and 1000 mg per unit dose.

8. A method of treating a central nervous system ailment related to the GABA uptake in a subject in need of such treatment comprising administering to said subject an effective amount of a compound according to claim 1.

9. A method of treating a central nervous system ailment related to the GABA uptake in a subject in need of such treatment comprising administering to said subject a pharmaceutical composition according to claim 6.

10. A compound of formula I

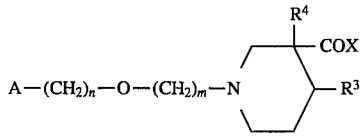

wherein

R³ and R⁴ each represents hydrogen or may together represent a bond;

X is hydroxy or $C_{1-4}$-alkoxy;

n is 0, 1 or 2;

m is 2, 3 or 4; and

A is

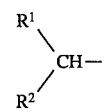

wherein

R¹ is a saturated or unsaturated five or six-membered carbocyclic ring optionally substituted with one or two halogen(s), straight or branched $C_{1-4}$-alkyl, phenyl, $C_{1-4}$-alkyl substituted with phenyl or $C_{2-4}$-alkenyl substituted with phenyl wherein the phenyl groups may be optionally substituted with halogen, $C_{1-4}$-alkyl, $C_{1-4}$-alkoxy or trifluoromethyl and wherein the saturated or unsaturated five or six-membered carbocyclic ring may be optionally fused with a benzo ring; and R² is hydrogen, straight or branched $C_{1-8}$-alkyl, or straight or branched $C_{2-8}$-alkenyl; or a pharmaceutically acceptable salt thereof.

11. A compound according to claim 10, wherein the carbocyclic ring is substituted with phenyl which is optionally substituted with halogen, $C_{1-4}$-alkyl, $C_{1-4}$-alkoxy or trifluoromethyl.

12. A compound according to claim 10, wherein the carbocyclic ring is fused with a benzo ring.

13. A compound according to claim 10 which is 1-(2-(3-Phenyl-1-propyloxy)ethyl)-3-piperidinecarboxylic acid or a pharmaceutically acceptable salt thereof.

14. A compound according to claim 10 which is (R)-1-(2-(2-Benzylbenzyloxy)ethyl)-3-piperidinecarboxylic acid or a pharmaceutically acceptable salt thereof.

15. A compound according to claim 10 which is (R)-1-(2-((1-Phenyl-2-naphthyl)methoxy)ethyl)-3-piperidinecarboxylic acid or a pharmaceutically acceptable salt thereof.

16. A compound according to claim 10 which is (R)-1-(2-(2-Phenylbenzyloxy)ethyl)-3-piperidinecarboxylic acid or a pharmaceutically acceptable salt thereof.

17. A compound according to claim 10 which is (R)-1-(2-(2-(2-Benzylphenyl)ethoxy)ethyl)-3-piperidinecarboxylic acid or a pharmaceutically acceptable salt thereof.

18. A compound according to claim 10 which is (R)-1-(2-(3-Benzylbenzyloxy)ethyl)-3-piperidinecarboxylic acid or a pharmaceutically acceptable salt thereof.

19. A compound according to claim 10 which is (R)-1-(2-(2-(Biphenyl-2-yl)ethoxy)ethyl)-3-piperidinecarboxylic acid or a pharmaceutically acceptable salt thereof.

20. A pharmaceutical composition comprising a compound according to claim 10 together with a pharmaceutically acceptable carrier or diluent.

21. The pharmaceutical composition according to claim 20, wherein the compound is present in an amount between 0.5 mg and 1000 mg per unit dose.

22. A method of treating a central nervous system ailment related to the GABA uptake in a subject in need of such treatment comprising administering to said subject an effective amount of a compound according to claim 10.

23. A method of treating a central nervous system ailment related to the GABA uptake in a subject in need of such treatment comprising administering to said subject a pharmaceutical composition according to claim 20.

24. A compound of formula I

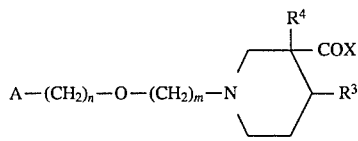 (I)

wherein

R³ and R⁴ each represents hydrogen or may together represent a bond;

X is hydroxy or $C_{1-4}$-alkoxy;

n is 0, 1 or 2;

m is 2, 3 or 4; and

A is

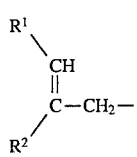

wherein

R¹ is a saturated or unsaturated five or six-membered carbocyclic ring optionally substituted with one or two halogen(s), straight or branched $C_{1-4}$-alkyl, phenyl, $C_{1-4}$-alkyl substituted with phenyl or $C_{2-4}$-alkenyl substituted with phenyl wherein the phenyl groups may be optionally substituted with halogen, $C_{1-4}$-alkyl, $C_{1-4}$-alkoxy or trifluoromethyl and wherein the saturated or unsaturated five or six-membered carbocyclic ring may be optionally fused with a benzo ring; and R² is hydrogen, straight or branched $C_{1-8}$-alkyl, or straight or branched $C_{2-8}$-alkenyl; or a pharmaceutically acceptable salt thereof.

25. A compound according to claim 24, wherein the carbocyclic ring is substituted with phenyl which is optionally substituted with halogen, $C_{1-4}$-alkyl; $C_{1-4}$-alkoxy or trifluoromethyl.

26. A compound according to claim 24, wherein the carbocyclic ring is fused with a benzo ring.

27. A compound according to claim 24 which is E-(R)-1-(2-((2,3-Diphenyl-2-propen-1-yl)oxy)ethyl)-3-piperidinecarboxylic acid or a pharmaceutically acceptable salt thereof.

28. A compound according to claim 24 which is Z-(R)-1-(2-((2,3-Diphenyl-2-propen-1-yl)oxy)ethyl)-3-piperidinecarboxylic acid or a pharmaceutically acceptable salt thereof.

29. A pharmaceutical composition comprising a compound according to claim 24 together with a pharmaceutically acceptable carrier or diluent.

30. The pharmaceutical composition according to claim 29, wherein the compound is present in an amount between 0.5 mg and 1000 mg per unit dose.

31. A method of treating a central nervous system ailment related to the GABA uptake in a subject in need of such treatment comprising administering to said subject an effective amount of a compound according to claim 24.

32. A method of treating a central nervous system ailment related to the GABA uptake in a subject in need of such treatment comprising administering to said subject a pharmaceutical composition according to claim 29.

* * * * *